(12) United States Patent
Strickler et al.

(10) Patent No.: US 7,737,060 B2
(45) Date of Patent: Jun. 15, 2010

(54) MEDICAL DEVICES CONTAINING MULTI-COMPONENT FIBERS

(75) Inventors: Frederick H. Strickler, Natick, MA (US); Barron Tenney, Haverhill, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 309 days.

(21) Appl. No.: 11/395,964

(22) Filed: Mar. 31, 2006

(65) Prior Publication Data

US 2007/0232169 A1  Oct. 4, 2007

(51) Int. Cl.
| | |
|---|---|
| B32B 5/02 | (2006.01) |
| B32B 27/12 | (2006.01) |
| B32B 15/14 | (2006.01) |
| A61F 2/01 | (2006.01) |
| A61F 2/02 | (2006.01) |
| A61F 2/82 | (2006.01) |
| A61F 13/00 | (2006.01) |

(52) U.S. Cl. ............ 442/361; 442/123; 442/199; 442/200; 442/201; 442/202; 442/228; 442/229; 442/238; 442/362; 442/363; 442/364; 442/365; 442/376; 442/377; 602/44; 602/45; 604/891.1; 604/93.01; 606/228; 606/230; 606/908; 606/910

(58) Field of Classification Search .......... 428/364, 428/365, 373, 374; 442/1–2, 4, 35–36, 50–51, 442/57, 164–171, 199–202, 239, 268, 271, 442/272, 274, 301, 361–365, 381, 382, 389, 442/400–403, 409, 411, 414, 417; 602/41–79; 604/358, 365, 367, 370–372

See application file for complete search history.

(56) References Cited

U.S. PATENT DOCUMENTS

| | | | |
|---|---|---|---|
| 4,044,404 A | 8/1977 | Martin et al. | 3/19 |
| 4,370,114 A | 1/1983 | Okamoto et al. | 425/131.5 |
| 4,381,274 A | 4/1983 | Kessler et al. | 264/147 |
| 4,475,972 A | 10/1984 | Wong | 156/167 |
| 4,738,740 A | 4/1988 | Pinchuk et al. | 156/167 |
| 4,743,252 A | 5/1988 | Martin, Jr. et al. | 623/1 |
| 4,842,505 A | 6/1989 | Annis et al. | 425/174.8 E |
| 5,162,074 A | 11/1992 | Hills | 156/644 |

(Continued)

FOREIGN PATENT DOCUMENTS

EP    0668083 A1    8/1995

(Continued)

OTHER PUBLICATIONS

Annis et al, "An Elastomeric Vascular Prothesis," *Trans. Am. Soc. Artif. Intern. Organs*, vol. XXIV, pp. 209-214 (1978).

(Continued)

*Primary Examiner*—Jennifer A Chriss
(74) *Attorney, Agent, or Firm*—Mayer & Williams PC; David B. Bonham; Keum J. Park

(57) ABSTRACT

According to an aspect of the present invention, medical devices are provided that contain at least one multi-component polymeric fiber. The multi-component polymeric fiber further contains at least two components of differing composition.

35 Claims, 4 Drawing Sheets

U.S. PATENT DOCUMENTS

| | | | |
|---|---|---|---|
| 5,344,297 A | 9/1994 | Hills | 425/131.5 |
| 5,468,574 A | 11/1995 | Ehrenberg et al. | 429/33 |
| 5,549,663 A | 8/1996 | Cottone, Jr. | 623/1 |
| 5,733,925 A | 3/1998 | Kunz et al. | 514/449 |
| 5,840,387 A | 11/1998 | Berlowitz-Tarrant et al. | 428/36.91 |
| 5,855,598 A | 1/1999 | Pinchuk | 623/1 |
| 6,162,537 A * | 12/2000 | Martin et al. | 428/373 |
| 6,545,097 B2 | 4/2003 | Pinchuk et al. | 525/240 |
| 6,551,353 B1 | 4/2003 | Baker et al. | 623/1.42 |
| 6,596,296 B1 | 7/2003 | Nelson et al. | 424/426 |
| 6,605,294 B2 * | 8/2003 | Sawhney | 424/426 |
| 6,753,071 B1 * | 6/2004 | Pacetti | 428/212 |
| 6,767,498 B1 | 7/2004 | Talley, Jr. et al. | 264/474 |
| 6,803,102 B1 | 10/2004 | Talley, Jr. et al. | 428/373 |
| 6,833,104 B2 | 12/2004 | Berger | 264/555 |
| 6,861,142 B1 | 3/2005 | Wilkie et al. | 428/373 |
| 7,105,018 B1 * | 9/2006 | Yip et al. | 623/1.15 |
| 7,481,835 B1 * | 1/2009 | Pacetti et al. | 623/1.15 |
| 2001/0023020 A1 | 9/2001 | Martin et al. | 428/373 |
| 2002/0052612 A1 | 5/2002 | Schmitt et al. | 606/151 |
| 2003/0078647 A1 | 4/2003 | Vallana et al. | 623/1.11 |
| 2003/0134099 A1 | 7/2003 | Barrows | 428/297.4 |
| 2003/0199992 A1 | 10/2003 | Schmitt | 623/23.71 |
| 2004/0028655 A1 | 2/2004 | Nelson et al. | 424/93.2 |
| 2004/0030377 A1 | 2/2004 | Dubson et al. | 623/1.13 |
| 2004/0082239 A1 * | 4/2004 | Di Luccio et al. | 442/59 |
| 2004/0132376 A1 | 7/2004 | Haworth | 442/364 |
| 2004/0170830 A1 * | 9/2004 | Morton-Finger | 428/373 |
| 2005/0106211 A1 | 5/2005 | Nelson et al. | 424/423 |
| 2005/0208107 A1 | 9/2005 | Helmus et al. | 424/443 |

FOREIGN PATENT DOCUMENTS

| | | |
|---|---|---|
| EP | 1023879 A2 * | 8/2000 |
| WO | WO 0038590 A1 * | 7/2000 |
| WO | WO 02/49535 A2 * | 6/2002 |
| WO | 2004/098503 A2 | 11/2004 |

OTHER PUBLICATIONS

World Class Fiber Technology, seven pages of commercial material for Hills, Inc., downloaded from http://www.hillsinc.net on Jan. 5, 2007.

J.C. Cho et al., "Synthesis, characterization and drug release properties of poly(methyl methacrylate-*b*-isobutylene-*b*-methyl methacrylate) and poly(hydroxyethyl methacrylate-*b*isobutylene-*b*-dydroxyethyl methacrylate)", *Polymer Preprints* 2005, vol. 46(1), pp. 105-106.

Yossef A. Elabd and Eugene Napadensky, "Sulfonation and characterization of poly(styrene-isobutylene-styrene) triblock copolymers at high ion-exchange capacities", *Polymer* (2004) vol. 45 3037-3043.

International Search Report and Written Opinion issued in related application PCT/US2007/007778.

\* cited by examiner

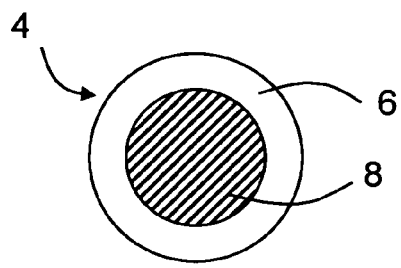
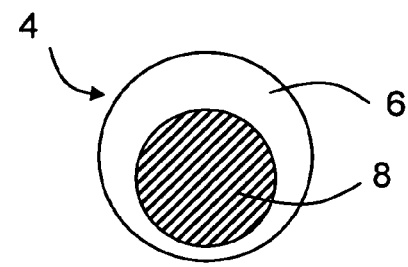
Fig. 1A (Prior Art)     Fig. 1B (Prior Art)
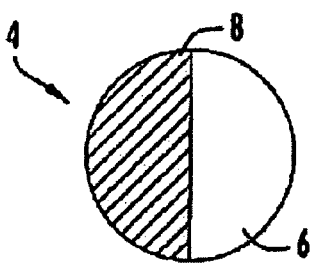
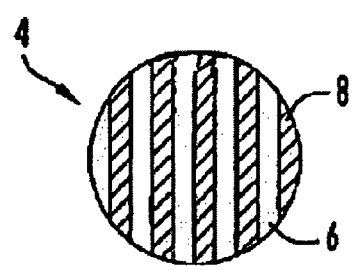
Fig. 1C (Prior Art)     Fig. 1D (Prior Art)
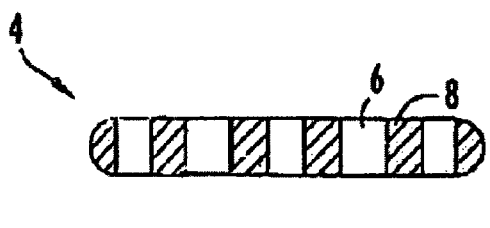
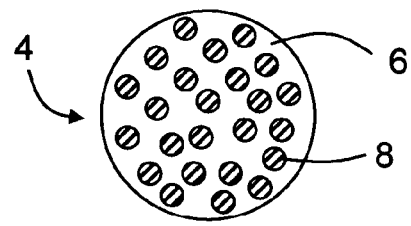
Fig. 1E (Prior Art)     Fig. 1F (Prior Art)
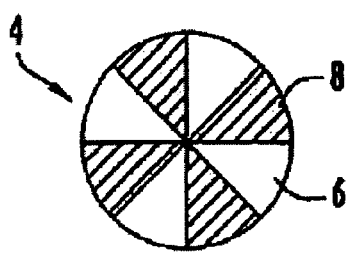
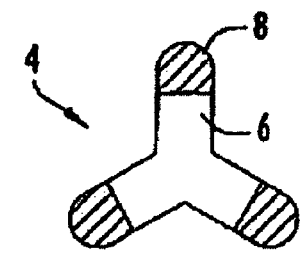
Fig. 1G (Prior Art)     Fig. 1H (Prior Art)

MEDICAL DEVICES CONTAINING MULTI-COMPONENT FIBERS

FIELD OF THE INVENTION

The present invention relates to medical devices that contain multi-component fibers.

BACKGROUND OF THE INVENTION

Fibers and collections of fibers have been used as materials in various applications in medicine and surgery ranging from sutures to wound dressings to skin grafts to arterial grafts, among many others. These applications are based on the unique properties of fibers as medical materials.

SUMMARY OF THE INVENTION

According to an embodiment of the invention, medical devices are provided that contain at least one multi-component polymeric fiber, which further contains at least two components of differing composition.

Advantages of the present invention are that medical devices may be provided which are closely tailored to the application at hand, for example, having tailored drug release rates, tailored biodegradation rates, tailored hydrophobic-hydrophilic balance and/or tailored surface area, among others.

These and other embodiments and advantages of the present invention will become immediately apparent to those of ordinary skill in the art upon review of the Detailed Description and Claims to follow.

BRIEF DESCRIPTION OF THE DRAWINGS

FIGS. 1A to 1K are cross-sectional views which schematically illustrate various known bi-component fiber structures.

DETAILED DESCRIPTION OF THE INVENTION

Figure 1I:
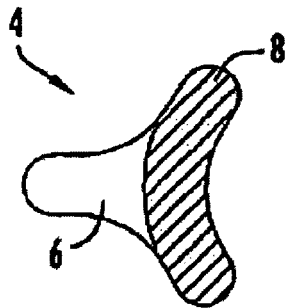

In various aspects of the invention, medical devices are provided, which contain one or more multi-component polymeric fibers.

As used herein, a "polymeric" object, such as a polymer fiber, is an object that contains polymers, commonly 50 wt % to 75 wt % to 90 wt % to 95 wt % to 99 wt % or more polymers.

As used herein, "polymers" are molecules containing multiple copies (e.g., from 2 to 5 to 10 to 25 to 50 to 100 to 250 to 500 to 1000 or more copies) of one or more constitutional units, commonly referred to as monomers. Polymers may take on a number of architectures, which may be selected, for example, from cyclic, linear and branched architectures. Branched architectures include star-shaped architectures (e.g., configurations in which three or more chains emanate from a single branch point), comb architectures (e.g., architectures having a main chain and a plurality of side chains), and dendritic architectures (e.g., arborescent and hyperbranched polymers), among others.

As used herein, "homopolymers" are polymers that contain multiple copies of a single constitutional unit. "Copolymers" are polymers that contain multiple copies of at least two dissimilar constitutional units, examples of which include random, gradient, periodic (e.g., alternating) and block copolymers. As used herein, "block copolymers" are copolymers that contain two or more polymer blocks that differ in composition, for instance, because a constitutional unit (i.e., monomer) is found in one polymer block that is not found in another polymer block. As used herein, a "polymer block" is a grouping of constitutional units (e.g., 2 to 5 to 10 to 25 to 50 to 100 to 250 to 500 to 1000 or more units). Blocks can be branched or unbranched. Blocks can contain a single type of constitutional unit (also referred to herein as "homopolymeric blocks") or they can contain multiple types of constitutional units (also referred to herein as "copolymeric blocks") which may be provided, for example, in a random, gradient, or periodic (e.g., alternating) distribution.

Polymeric fibers for the practice of the invention, including multi-component polymeric fibers, may be made by any suitable fiber forming technique, including, for example, melt spinning and solvent spinning (e.g., dry spinning and wet spinning). These processes typically employ extrusion nozzles having one or more orifices, also called distributors, jets or spinnerets. Fibers having a variety of cross-sectional shapes may be formed, depending upon the shape of the orifice(s). Some examples of fiber cross-sections include polygonal (e.g., triangular, rectangular, hexagonal, etc.), circular, oval, multi-lobed, and annular (hollow) cross-sections, among others. In melt spinning, polymers are heated to melt temperature prior to extrusion. In wet and dry spinning polymers are dissolved in a solvent prior to extrusion. In dry spinning, the extrudate is subjected to conditions whereby the solvent is evaporated, for example, by exposure to a vacuum or heated atmosphere (e.g., air) which removes the solvent by evaporation. In wet spinning the spinneret is immersed in a liquid, and as the extrudate emerges into the liquid, it solidifies. The resulting fiber is typically taken up on a rotating mandrel or another take-up device. During take up, the fiber may be stretched (i.e., drawn) to orient the polymer molecules. A common aspect to various spinning techniques, including those described above, is that a polymer containing liquid is extruded and ultimately solidified (e.g., due to cooling, solvent removal, chemical reaction, etc.).

In certain embodiments of the invention, electrostatic spinning processes may be employed. Electrostatic spinning processes have been described, for example, in Annis et al. in "An Elastomeric Vascular Prosthesis", Trans. Am. Soc. Artif. Intern. Organs, Vol. XXIV, pages 209-214 (1978), U.S. Pat. No. 4,044,404 to Martin et al., U.S. Pat. No. 4,842,505 to Annis et al., U.S. Pat. No. 4,738,740 to Pinchuk et al., and U.S. Pat. No. 4,743,252 to Martin Jr. et al. In electrostatic spinning, electrostatic charge generation components are employed to develop an electrostatic charge between the distributor (e.g., the spinneret) and the mandrel. For example, the mandrel may be grounded or negatively charged, while the distributor is positively charged. Alternatively, the distributor may be grounded or negatively charged, while the mandrel can be positively charged. The potential that is employed may be constant or variable. As a result of the electrostatic charge that is generated, the polymeric fibers experience a force that accelerates them from the distributor to the mandrel. Also, the fibers may have a tendency to flap, wobble and/or vibrate. Consequently, structures may be created which have smaller diameter fibers in a more random distribution, relative to the same structures formed in the absence of the electrostatic charge. Moreover, contact between the fibers may be enhanced, because the fibers are electrostatically drawn onto the mandrel, in some instances causing the fibers to sink to some extent into underlying fibers.

Fibers employed in the practice of the invention can vary widely in size, but are typically less than 50 microns (μm) across, for example, ranging from 50 microns to 25 microns to 10 microns to 5 microns to 2.5 microns to 1 micron to 0.5 micron (500 nm) to 0.25 micron (250 nm) to 0.1 micron (100 nm), or less.

As used herein, a "multi-component polymeric fiber" is a polymeric fiber within whose cross-section can be found at least two distinct cross-sectional components, each of different composition, for instance, (a) because the polymer content varies between the components, or (b) where one or more therapeutic agents are provided, because the therapeutic agent content varies between the components, or (c) because both the polymeric and therapeutic agent content varies between the components, among numerous other possibilities.

"Therapeutic agents," "drugs," "bioactive agents" "pharmaceuticals," "pharmaceutically active agents" and other related terms may be used interchangeably herein. Therapeutic agents may be used singly or in combination.

Polymer content may vary between components in various ways, including one or more of the following, among others: (a) one component may contain a polymer that is not found in another component, for example, the components may contain completely different types of polymer(s) (e.g., polystyrene vs. polyisobutylene), one component may contain one or more types of polymers in addition to the polymer(s) found in the other component (e.g., a blend of polystyrene and polyisobutylene vs. polystyrene), and so forth, (b) where the components contain the same combination of polymers (e.g., polystyrene and polyisobutylene), the ratio of these polymers may vary between the components, (c) where the components contain copolymers having the same monomer content (e.g., poly[styrene-co-isobutylene]), the ratio of the monomers within the copolymers may vary between the components and/or the distribution of the monomers within the copolymers (e.g., random vs. periodic vs. block, etc.) may vary between the components, and/or (d) where the components contain the same type of polymer (e.g., polystyrene or poly [styrene-co-isobutylene]), the molecular weight of the polymer and/or the architecture of the polymer may vary between the components.

Multi-component polymeric fibers for use in the present invention may be formed from biostable polymer components, biodegradable polymer components, or a combination of both. As defined herein, a "biostable" component is one which remains intact over the period that the medical device is intended to remain implanted within the body. Similarly, as defined herein, a "biodegradable" component is one which does not remain intact over the period which the medical device is intended to remain within the body, for example, due to dissolution, chemical breakdown, etc. of the component.

Variations in polymer content between the components may be accompanied by variation in a number of physical and chemical characteristics including the following, among many others: mechanical strength, hardness, surface tack, elasticity, water diffusivity, therapeutic agent diffusivity (where present), degradation rate (where biodegradable), and hydrophobic/hydrophilic nature (influencing, for example, wettability, as well as water diffusivity and therapeutic agent diffusivity, where present).

In embodiments of the invention in which multi-component fibers are employed that contain one or more therapeutic agents, the therapeutic agent content may vary between fiber components in the following ways, among others: (a) one component may contain a therapeutic agent whereas another component may not, (b) each component may contain differing therapeutic agents, (c) each component may contain a common therapeutic agent, with one component having an additional therapeutic agent, (d) each component may contain a common therapeutic agent, with each component having an additional differing therapeutic agent, and so forth.

Figure 1J:
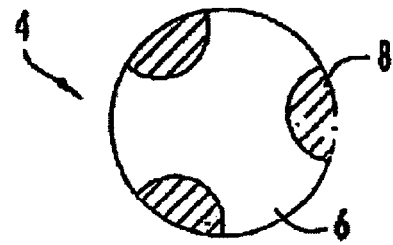
Figure 1K:
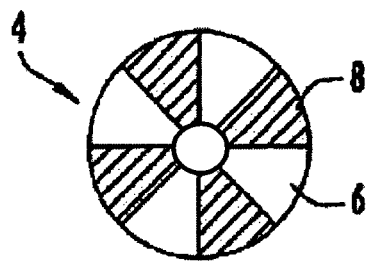

The simplest multi-component fibers are presumably bi-component fibers, within whose cross-section can be found two distinct cross-sectional components of different composition. Numerous types of bi-component fibers are known in the fiber making industry, including fibers 4 in which the first component 6 and second component 8 are arranged in concentric and eccentric sheath/core fiber structures (see, e.g., FIGS. 1A and 1B), side-by-side fiber structures (see, e.g., FIGS. 1C through 1E), island-in-sea fiber structures (see, e.g., FIG. 1F), pie wedge fiber structures (see, e.g., FIG. 1G), multilobal structures (see, e.g., FIGS. 1H and 1I), as well as essentially limitless other variations (see, e.g., FIG. 1J). Hollow versions of such fibers are also known (see, e.g., FIG. 1K).

Broadly, the bi-component fibers configurations shown in FIGS. 1A-1K fall into one of two groups: (1) a group in which the first and second components 6,8 both extend to the outside surface (e.g., FIGS. 1C, 1D, 1E, 1G, 1H, 1I, 1J and 1K) and (b) a group in which the first component 6 reaches the outside surface and the second component 8 is internal to the fiber (e.g., FIGS. 1A, 1B and 1F).

In the former group, mass transport of species into the first component (e.g., body fluids such as whole blood and serum) and mass transport of species out of the first component (e.g., therapeutic agent, if present, polymer breakdown products, if biodegradable, etc.) will depend, for example, on the chemical nature of the polymer(s) that are used to form the first component (e.g., based on the diffusivity of the species within the first component, based on the degradation rate of the first component, where biodegradable, etc.). Similarly, mass transport of species to and from the second component will depend, for example, on the chemical nature of the polymer(s) forming the second component. The nature of the polymer(s) forming the first component may also affect the transport of species to and from the second component, and vice versa. For example, where the polymer(s) forming the first component provide a low-resistance path for species to and from the second component (e.g., where the first component contains a swellable hydrogel or water soluble polymer), or where the first component is rapidly biodegraded, transport of species to and from the second component is likely to be increased.

In the latter group, because the first component lies between the second component and fiber exterior, mass transport of species between the second component and the exterior will clearly be regulated by the first component, for example, based on the diffusivity of the species within the first component, based on the degradation rate of the first component (e.g., the rate of chemical breakdown and/or dissolution, where biodegradable), and/or the hygroscopic nature of the first component (e.g., the degree and amount of swelling of the first component).

Thus, within a given bi-component fiber, the components may have, for example, a differing polymer content (e.g., one biodegradable and one biostable, both biostable with differing properties, both biodegradable with differing properties).

Moreover, the components may contain no therapeutic agent, the components may contain the same therapeutic agent(s) at the same or different dosages, the components may contain differing therapeutic agents, one component may contain one or more therapeutic agents and the other component may contain no therapeutic agent, and so forth. In addition, as indicated above, both components may extend to an outside surface of the polymer, or one component may extend to an outside surface of the fiber while the other does not. Furthermore, the bi-component fibers may have a variety of overall cross-sections, including circular, oval, polygonal, and multilobed cross-sections, among others.

Such flexibility provides the ability to tailor the composition and/or architecture of the fiber to the application at hand.

For instance, where the same therapeutic agent is used for each component, differences in polymer content between the components may be used to provide complex release profiles for the therapeutic agent, including the generation of an initial burst effect (i.e., the rapid release of large quantities of therapeutic soon after implantation or insertion, which may have significant therapeutic benefits) followed by a period of slower release, and bimodal release profiles, among others. Where differing therapeutic agents are used for each component, one agent may be quickly released to address short term issues and another to address longer term issues (e.g., for a vascular stent, it may be desirable to release agents for wound healing over a first time period, and to release antiproliferative agents over a longer time period). In another example where differing therapeutic agents are used, one relatively hydrophilic and one relatively hydrophobic, the agents may be matched with polymers of comparable hydrophilicity/hydrophobicity in order to achieve targeted therapeutic release rates. For example, a relatively hydrophilic agent may be provided in admixture with a relatively hydrophilic polymer in a first component, whereas a relatively hydrophobic agent may be provided in admixture with a relatively hydrophobic polymer in a second component or in admixture with a combination of relatively hydrophobic and relatively hydrophilic polymers in a second component, and so forth.

As a more specific example, a first component 6 may contain a polymer (e.g., SIBS, a triblock copolymer having a polyisobutylene midblock and polystyrene end blocks) with a first loading of a first therapeutic agent (e.g., 25%) and the second component 8 may contain the same polymer (e.g., SIBS) but with a lower loading (e.g., 10%) of the same therapeutic. This may help tailor the desired release rate by having a higher initial release followed by a more sustained release.

In another specific example, the first component 6 may contain a polymer (e.g., SIBS) and a first therapeutic agent (e.g., an anti-platelet or anti-thrombotic therapeutic agent), while the second component 8 contains the same polymer and a different therapeutic agent (e.g., an anti-proliferative agent). With a copolymer such as SIBS, the monomer ratio (e.g., the ratio of styrene to isobutylene) may also be varied to tailor the release profile of the therapeutic agents.

In yet another specific example the first component 6 contains a first therapeutic agent and a first biostable polymer (e.g., SIBS), while the second component 8 contains the a second therapeutic agent a second biostable polymer (e.g., poly(methyl methacrylate)-b-polyisobutylene-b-poly(methyl methacrylate) triblock copolymer (PMMA-b-PIB-b-PMMA) or poly(hydroxyethyl methacrylate)-b-polyisobutylene-b-poly(hydroxyethyl methacrylate) (PHEMA-b-PIB-b-PHEMA). The first and second therapeutic agents may be the same (e.g., an anti-proliferative agent) or different (e.g., an anti-thrombotic and an anti-proliferative agent). For example, it has been observed that the release profile of paclitaxel from each of these copolymers is different from that of the others. See J. C. Cho et al., "Synthesis, characterization and drug release properties of poly(methyl methacrylate-b-isobutylene-b-methyl methacrylate) and poly(hydroxyethyl methacrylate-b-isobutylene-b-hydroxyethyl methacrylate), *Polymer Preprints* 2005, 46(1), 105.

In a further specific example, one component contains a biodegradable polymer (e.g., such as PLGA, poly(d,l-lactide-co-glycolide)) and a first therapeutic agent and the other component contains a biostable polymer (e.g., SIBS) and a second therapeutic agent. The first and second therapeutic agents may be the same (e.g., an anti-proliferative agent) or different (e.g., anti-thrombotic agent and an anti-proliferative agent). The release rate of the therapeutic agent from the component that contains the biodegradable polymer may depend on the degradation rate of the biodegradable polymer. Moreover, after degradation of the biodegradable polymer is complete, the fiber 4 now consists of a single biostable component, which may have an increased surface area. See, e.g., FIG. 1G and FIG. 1J (where the second component 8 is biodegradable). In some instances, multiple fibers may be produced upon degradation. See, e.g., FIG. 1D, FIG. 1E, FIG. 1F, FIG. 1H, FIG. 1J and FIG. 1K (where the first component 6 is biodegradable).

For bicomponent fibers in which the first component 6 reaches the outside surface and the second component 8 is internal to the fiber (e.g., FIGS. 1A, 1B and 1F), the first component 6 may contain a first therapeutic agent and hydrophilic polymer (e.g., a hydrogel) that softens and swells in the presence of body fluids. The second component 8, on the other hand, may contain a second therapeutic agent and biostable polymer, such as, SIBS, (PMMA-b-PIB-b-PMMA), or (PHEMA-b-PIB-b-PHEMA), among others, depending on the desired release rate of the therapeutic. As above, the first and second therapeutic agents may be the same (e.g., an anti-proliferative agent) or different (e.g., an anti-thrombotic agent and an anti-proliferative agent). For example, the initial swelling of the hydrogel would allow for an initial burst of the first therapeutic, while also allowing the second therapeutic agent in the second component 8 to diffuse through the first component 6 to the surface. The hydrogel could be, for example, a thermoplastic hydrogel, such as poly(dimethylacrylamide-graft-polystyrene), which may be made by the free-radical polymerization of dimethylacrylamide and methacrylate-terminated polystyrene.

As indicated above, the first component 6 may contain a biodegradable polymer, such as, PLGA, where the degradation rate will influence the release rate of a therapeutic within the second component 6. The second component 8 may contain, for example, a biostable polymer, such as SIBS, (PMMA-b-PIB-b-PMMA) or (PHEMA-b-PIB-b-PHEMA), among others, depending on the desired release rate of the therapeutic (e.g., an anti-proliferative drug, such as paclitaxel). The influence of the first component 6 on release is particularly emphatic where the first component 6 reaches the outside surface and the second component 8 is internal to the fiber (e.g., FIGS. 1A, 1B and 1F). As also indicated above, multiple fibers will arise from a single fiber like that of FIG. 1F upon biodegradation of the first component 6.

Figure 2A:
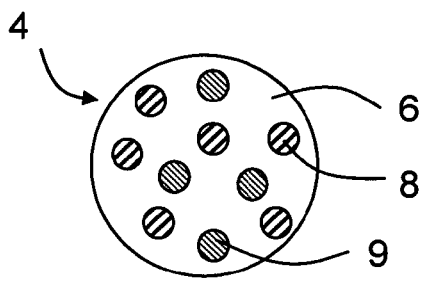
FIGS. 2A to 2D are cross-sectional views which schematically illustrate various tri-component fiber structures.
Figure 2B:
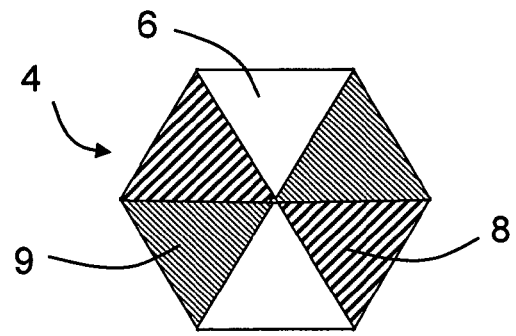
Figure 2C:
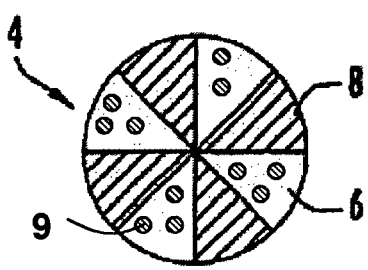

Of course, with a third component one could have many additional options such as (a) fibers in which the first 6, second 8 and third 9 components all extend to an outside surface of the fiber (e.g., a pie fiber structure, with three types of wedges, for example the hexagonal fiber cross-section of FIG. 2B), (b) fibers in which the first component 6 extends to an outside surface of the fiber and the second and third components 8 and 9 are internal to the fiber (see, e.g., FIG. 2A and FIG. 2D), and (c) fibers in which the first 6 and second 8 components extend to an outside surface of the fiber and the third component 9 is internal to the fiber (see, e.g., FIG. 2C), among many other possibilities.

For example, for a tri-component fiber, where differing therapeutic agents are used for each component, one agent may be quickly released to address short term issues, another to address intermediate term issues, and another to address long term issues (e.g., for a vascular stent, it may be desirable to release agents for anti-fouling over a first time period, to release antiproliferative agents over a longer time period, and to release agents to enhance endothelialization over an even longer time period).

Figure 2D:
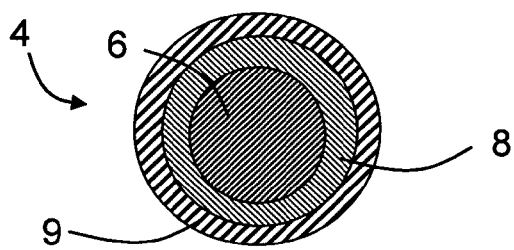

Such a concept may be embodied, for example, as shown in FIG. 2D, which illustrates a fiber 4 having a core component 6, an intermediate component 8 surrounding the core 6, and an outer component 9 surrounding the intermediate component 8. For example, the outer component 9 may contain an anti-thrombotic or anti-fouling agent (e.g., heparin), the intermediate component may contain paclitaxil (an anti-proliferative agent), and the core component 6 may contain an RDG peptide-containing species (a bioactive agent). The arrangement of the therapeutics outside to inside may help control at what rate and when the therapeutic agent is released (i.e., the therapeutic agent release profile), for example, under circumstances (a) where the core component 6, intermediate component 8, and outer component 9 each contains a biodegradable polymer, (b) where the intermediate component 8 and outer component 9 each contains a biodegradable polymer, and the core component 6 contains a biostable polymer, (c) where the outer component 9 contains a biodegradable polymer, the intermediate component 8 contains a hydrogel polymer, and the core component 6 contains a biostable polymer, and so forth.

Figure 3:
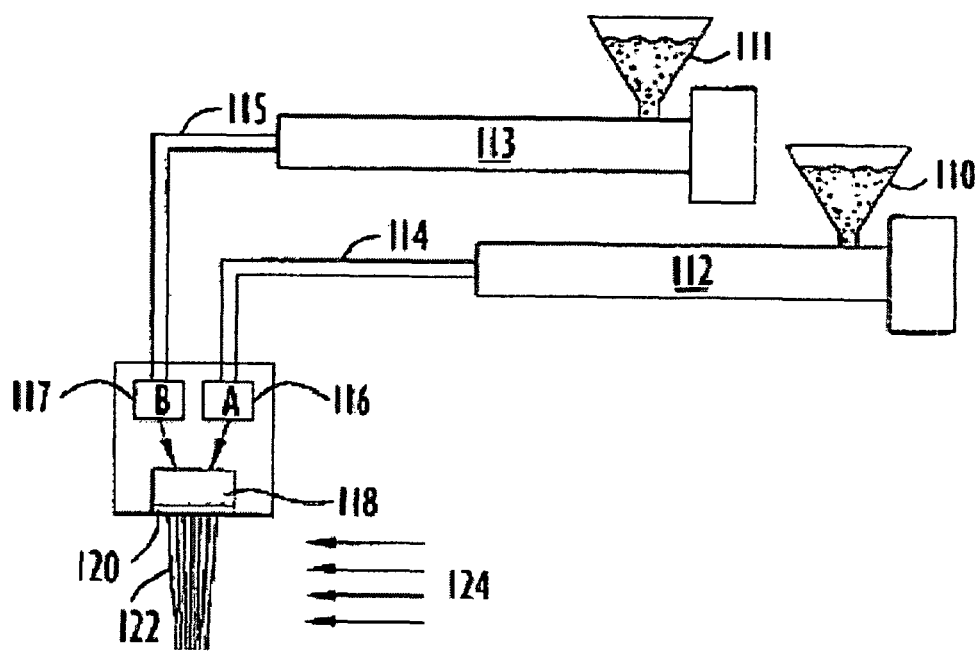
FIG. 3 is a schematic illustration of a known system for producing bi-component fibers.

An example of a system 100 for thermally (melt) producing multi-component fibers (specifically, bi-component fibers) may be found, for example, in FIG. 3. Turning now to FIG. 3, the system 100 includes a first hopper 110 into which pellets of a polymer component A are placed. The polymer is fed from hopper 110 to screw extruder 112, where the polymer is melted. The molten polymer flows through heated pipe 114 into metering pump 116 and spin pack 118. A second hopper 111 feeds a polymer component B into a screw extruder 113, which melts the polymer. The molten polymer flows through heated pipe 115 and into a metering pump 117 and spin pack 118. Spin pack 118 includes a spinneret 120 with orifices through which bi-component fibers 122 are extruded. One example of a suitable spin pack that may be utilized for the formation of bi-component fibers is described in U.S. Pat. No. 5,162,074 to Hills. The extruded fibers 122 emerging from the spinneret are quenched with a quenching medium 124 (e.g., air) and are directed, for example, onto a spinning mandrel (not shown) or any other suitable take-up arrangement.

Figure 4:
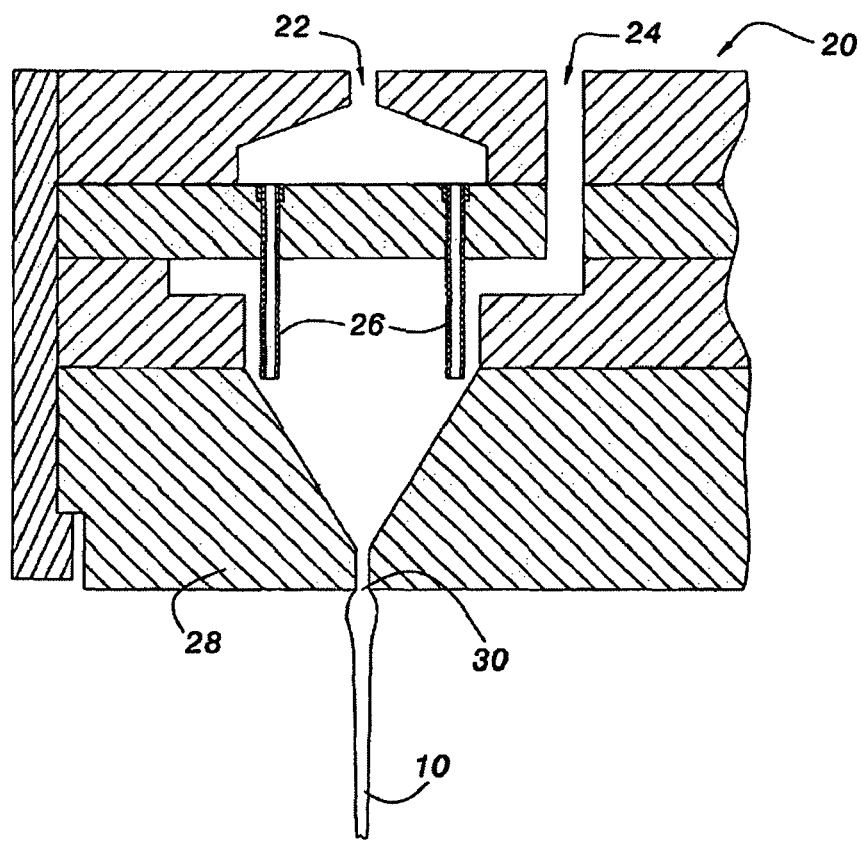
FIG. 4 is a schematic cross-sectional view of a known spin pack for generating a bi-component islands-in-the-sea fiber.

A cross-sectional view of a spin pack 20 which is suitable for generating a bi-component islands-in-the-sea fiber 10 is illustrated in FIG. 4. Spin pack 20 includes upstream openings 22 and 24 through which the island polymer and sea polymer respectively enter spin pack 20. The island polymer travels through capillary tubes 26 which inject the island polymer into the flow of the sea polymer at the entrance to spinneret 28 in various discrete locations along the edge of the spinneret entrance (only two locations are shown in the cross-section, but more are present along the edge of the spinneret entrance). The polymers flow through the spinneret 28 to an orifice 30, where they are extruded as an islands-in-the-sea fiber 10.

While only two polymer component streams are depicted in FIGS. 3 and 4, it is noted that systems may be configured for processing any selected number of polymer streams (e.g., three, four, five or more) depending upon the desired fiber configuration. Moreover, although melt spinning is specifically used to form the fibers in these drawings, other types of fiber spinning processes may be employed, including dry spinning, wet spinning, and chemical-reaction-based spinning, among others.

Further information concerning multi-component fiber spinning processes can be found, for example, in U.S. Pat. No. 4,381,274 to Kessler et al., U.S. Pat. No. 4,370,114 to Okamoto et al., U.S. Pat. No. 5,162,074 to Hills, U.S. Pat. No. 5,344,297 to Hills, U.S. Pat. No. 6,551,353 to Baker et al., U.S. Pat. No. 6,767,498 to Talley Jr. et al., U.S. Pat. No. 6,803,102 to Talley et al., U.S. Pat. No. 6,833,104 to Berger, U.S. Pat. No. 6,861,142 to Wilkie et al.

Medical devices that may be formed using multi-component fibers in accordance with the present invention are varied and include two-dimensional (i.e., open volume) structures and three-dimensional (i.e., closed volume) structures, among others. They may be formed using any suitable fiber-based construction technique including, for example, various woven and non-woven (e.g., knitted, braided, coiled, randomly wrapped, etc.) techniques. Examples of non-woven techniques include those that utilize thermal fusion, fusion due to removal of residual solvent, mechanical entanglement, chemical binding, adhesive binding, and so forth.

A specific example of a non-woven technique for forming three-dimensional structures from fibers is described in U.S. Pat. No. 4,475,972, in which articles are made by a procedure in which fibers are wound upon a mandrel and overlying fiber portions are simultaneously bonded with underlying fiber portions, which method may be adapted to the present invention.

For instance, two polymer solutions may be co-extruded from a spin pack, which may include one or more extrusion orifices, and which may produce bi-component fibers having any of a variety of designs as discussed above (e.g., fibers having circular, oval, polygonal, multi-lobed or irregular circumferences, among others, and having sheath/core, side-by-side, islands-in-sea, or pie wedge cross-sections, among others). The resulting fibers are wound onto a rotating mandrel, for example, as the spin pack reciprocates back and forth relative to the mandrel, or vice versa. Such activity will result in combined rotational and translational movement between the spin pack and the mandrel. The drying parameters (e.g., drying environment, solution temperature and concentration, spinneret-to-mandrel distance, etc.) may be controlled such that some residual solvent remains in the fibers as they are wrapped upon the mandrel. Upon further solvent evaporation, the overlapping fibers on the mandrel become bonded to each other, for example, at various locations where the fibers intersect or otherwise contact each other. Such fiber-to-fiber bonding results when the solvent-containing, partially-solidified fibers engage one another during winding. This engagement may be enhanced, for example, by drawing the extruded fibers (e.g., by selecting appropriate conditions that will uptake the fibers at a speed that is faster than the rate by which they are extruded from the spin pack), by formulating the polymer solution to have an particularly high solvent concentration and/or a less volatile solvent, and so forth. These activities also typically reduce the diameter of the fiber.

The size and/or shape of pores that are defined by the fibers may be controlled, for instance, by controlling the angle at which the fibers are wrapped upon the mandrel (which depends, for example, on the winding speed of the mandrel relative to the reciprocation speed of the distributor, etc.), by controlling the diameter of the fibers (which depends, for example, on the flow rate of the polymer solution through the spinneret orifice(s), the draw rate, the solvent content of the polymer solution, etc.), by controlling the degree of flattening of the fibers (e.g., through the use of higher or lower solvent content), and so forth.

The thickness of the fibrous region that is produced on the mandrel may be controlled, for instance, by varying the length of the fiber wound on the mandrel, by varying the width of the individual fibers, by varying the amount of solvent in the fiber (e.g., if the fiber is wet it may flatten and it may sink into the underlying layer, requiring more fiber passes to reach a desired thickness), and so forth.

Fiber spinning processes analogous to the above described solvent-based spinning, including melt- and chemical-reaction-based fiber spinning, may also be employed, in which single- or multi-component fibers are taken up on a rotating mandrel and become bonded to one another, for instance, because they are not quite solidified at the time of arrival at the mandrel (e.g., because they are not completely cooled, because chemical reactions such as cross-linking reactions within the fibers are not complete, etc.).

Using these and other techniques, fibrous regions containing single- and/or multi-component fibers may be formed. As used herein, a "fibrous region" is a region that contains fibers, typically 50 wt % to 75 wt % to 90 wt % to 95 wt % or even more fibers.

Pore size may vary widely in such regions, ranging from less than 1 micron to 1 micron to 2 microns to 5 microns to 10 microns to 25 microns to 50 microns to 100 microns or more. Where pore size is given it is the number average pore width and may be measured, for example, using optical microscopy or scanning electron microscopy (SEM). Pores need not be cylindrical. For example, in many embodiments of the invention, porous regions are formed from fibers that overlap at various angles and therefore appear to be randomly distributed and sized upon examination by microscopy.

In certain embodiments, two or more fibrous regions are provided within the medical devices of the invention. For example, a first fibrous layer may be provided on a first surface configured for contact with a first environment and a second fibrous layer may be provided on an opposing second surface configured for contact with a second environment. For instance, one fibrous layer may be provided on a luminal surface of a tubular medical device (e.g., a blood contacting surface of a stent or vascular graft or a digestive-fluid contacting surface of a gastrointestinal prosthesis), and another fibrous layer may be provided on the abluminal surface of the device, thus interfacing with a surrounding soft tissue environment, for instance, a vascular wall, perigraft tissue, or a body cavity (e.g., the peritoneal cavity). As another example, one fibrous layer may be provided on a tissue contacting surface of a two dimensional medical device (e.g., a colonic patch or heart patch), while the other fibrous layer may be provided on the opposing surface of the device, thus interfacing with a surrounding soft tissue environment or body cavity (e.g., the peritoneal tissue cavity or pericardium cavity). (Note that while certain specific examples described in the present application are directed to vascular prosthesis or gastrointestinal prosthesis, which includes prosthesis for the mouth, pharynx, esophagus, stomach, small intestine, large intestine, rectum and anus, as seen below, the medical devices of the invention are not so restricted, and will find use throughout the body.)

The medical devices of the present invention may also contain one or more polymeric barrier layers. Polymeric barrier layers may be formed by a variety of processes. For example, polymeric barrier layers may be formed from polymer containing fluids, such as polymeric solutions or polymeric melts, by applying the polymer containing fluid to an underlying template (e.g., a fibrous layer such as those described above or a template from which the resulting layer may be removed, such as a mold, mandrel etc.). Polymer containing fluids may be applied, for example, by various application techniques, including, for example, dip coating, spray coating, spin coating, web coating, and so forth, with multiple applications being possible.

For example, a polymer containing fluid may be applied to a mandrel before or after the formation of a fibrous layer such as those described above. Where the polymer containing fluid is to be applied to a fibrous layer, the fibrous layer may be removed from the mandrel prior to application of the polymer containing fluid (e.g., by dip coating, etc.), or it may remain on the mandrel during application (e.g., by spray coating, etc.).

As another example, polymeric barrier layers may be provided using fiber spinning processes, such as those described above, under conditions where the pores are sufficiently small to perform a barrier capacity (e.g., a barrier having pores less than one micron as a barrier to erythrocytes).

In some embodiments, fibrous layers in accordance with the present invention may be provided over all or a portion of an underlying medical device substrate. For example, in the case of a tubular medical device substrate (e.g., a stent, etc.), a fibrous layer may be provided over at least a portion of the inner luminal surface of the device, over at least a portion of the outer abluminal surface of the device, or both.

An advantage of providing a fibrous layer over the outer abluminal surface of a stent is that this will allow one or more therapeutic agents within the fibrous layer (e.g., agents for wound healing and/or antiproliferative agents) to migrate into the surrounding tissue (e.g., to promote wound healing and/or help prevent restenosis). The lumenal side of the stent, on the other hand, will be bare metal, which should promote healing (endothelial cell growth), since no antiproliferative drug is present on the lumenal side of the stent. Moreover, the lack of a polymer on the luminal side of the stent will generally reduce balloon withdrawal resistance during stent deployment procedures.

In other embodiments, one or more reinforcement elements may be provided within the medical devices of the invention, for instance, to improve the strength of the devices. For example, with tubular medical devices such as vascular prosthesis, such reinforcement elements may be provided to increase kink and/or compression resistance (e.g., to improve short and long term patency). Such reinforcement elements may be provided at the inner luminal surface, at the outer abluminal surface, and/or somewhere between the inner and outer surfaces (e.g., between inner and outer fibrous layers).

In various embodiments, it is desirable to provide a device which is strong, yet flexible (e.g., to facilitate surgical handling). For this purpose, elastic substrates and reinforcement elements may be selected. As defined herein an elastic material is one which can elastically recover from tension, compression, torsion and/or bending, with minima plastic/permanent deformation. Typically, elastic materials have an elastic modulus (modulus of elasticity) that ranges, for example, from on the order of 1,000 MPa (for a polymer) to 2500 MPa to 5,000 MPa to 10,000 MPa to 25,000 MPa to 50,000 MPa, to 100,000 MPa to 250,000 MPa (for a hard metal).

A variety of materials may be used as substrates and reinforcement elements, assuming that they have the proper mechanical characteristics and that they do not adversely affect biocompatibility of the medical device to a significant degree. Materials include non-metallic materials such as homopolymers, copolymers, polymer blends, and polymer composites (e.g., formed using various polymers and bioengineering plastics, such as polypropylene, FEP, PEEK, etc.). Materials also include metallic materials, such as metals (e.g. Ti, Ta), metal alloys comprising iron and chromium (e.g., stainless steels, including platinum-enriched radiopaque stainless steel), alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N) and alloys comprising cobalt, chromium, tungsten and nickel (e.g., L605), alloys comprising nickel and chromium (e.g., inconel alloys), as well as composite reinforcement elements made using the forgoing. Materials having both super elastic and shape-memory characteristics, for example, alloys comprising nickel and titanium (e.g., Nitinol) may be beneficial in certain embodiments.

Medical device substrates will, of course, vary widely in shape and size, as will reinforcement elements. For example, these may be selected, for example, from hollow structures such as balloons and tubing, including laser cut, plasma etched or chemically etched tubing, from sheets including laser cut, plasma etched or chemically etched sheets (which may be, for example, rolled into a tube and welded), and from filamentous elements (which term may be used interchangeably herein with other like terms such as filaments, fibers, wires, ribbons, and so forth), among many others. Filaments may be employed, for example, as a series of hoops, as woven, braided, knitted, coiled, or random filamentous cylinders (which may be welded or otherwise interconnected, as desired), and so forth.

As can be appreciated from the foregoing, a wide variety of medical devices may be formed in accordance with the present invention including closed-volume (hollow) medical devices, such as tubular articles (e.g., vascular and non-vascular grafts and stent grafts, including large and small vascular grafts such as coronary artery bypass grafts, peripheral vascular grafts and endovascular grafts, other tubular structures such as biliary, urethral, ureteral, intestinal and esophageal tubular structures, etc.), as well as various open-volume medical devices such as vascular and non-vascular patches (e.g., patches for wound healing, patches for hernia repair and patches for the gastrointestinal tract and the urogenital system). Further examples of medical devices include vascular and non-vascular tissue scaffolding, vascular and non-vascular closure devices, for example devices for closure of peripheral and arterio-venous fistula, sutures, meshes, valve leaflets for heart valves and venous valves, vascular access devices including vascular access ports and arterio-venous access grafts (e.g., devices which are utilized to give frequent arterial and/or venous access such as for antibiotics, total parental nutrition, intravenous fluids, blood transfusion, blood sampling, or arterio-venous access for hemodialysis, and so forth), embolic filters (e.g., distal protection filters), uterine slings, fabric to join LVADs (left ventricular assist devices) and TAHs (total artificial hearts) to human arteries, and so forth.

Moreover, fibrous coating layers may be provided over substrates corresponding to a wide variety devices, in addition to those above, including, for example, catheters (e.g., renal or vascular catheters such as balloon catheters and various central venous catheters), guide wires, balloons, embolization devices including cerebral aneurysm filler coils (including Guglilmi detachable coils and metal coils), pacemakers and pacemaker leads, defibrillation leads and coils, left ventricular assist hearts and pumps, total artificial hearts, anastomosis clips and rings, and cannulae.

In some embodiments, the medical devices of the invention are suitable for long-term implantation. As used herein, "long-term" implantation means implantation periods greater than 30 days, for example, ranging from 1 month to 3 months to 6 months to 12 months to 24 months or even longer, including the remaining lifetime of the patient.

In instances where hollow (including tubular) medical devices are provided to reinforce, repair or replace a body lumen (e.g., stents, grafts, stent grafts, patches etc.), their dimensions may be tailored to approximate the dimensions of all or a portion of the body lumen. Examples of body lumens include lumens of the cardiovascular system such as the heart, arteries and veins (e.g., coronary, femoral, aorta, ilial, carotid and vertebro-basilar arteries), lumens of the genitourinary system such as the urethra (including prostatic urethra), bladder, ureters, vagina, uterus, spermatic and fallopian tubes, the nasolacrimal duct, the eustachian tube, lumens of the respiratory tract, such as the trachea, bronchi, nasal passages and sinuses, lumens of the gastrointestinal tract such as the esophagus, gut, duodenum, small intestine, large intestine, colon, biliary and pancreatic duct systems, lumens of the lymphatic system, and so forth.

Hence, hollow medical devices (including any tubular shape, such as those having circular and elliptical cross-sections) for use in the present invention may vary widely in diameter, for example, ranging from 0.5 mm to 1 mm to 2 mm to 5 mm to 10 mm to 20 mm to 50 mm or more in diameter. For instance, tubular articles having diameters ranging from 0.5 to 2 mm may be employed for microvascular work and conduits for nerve regeneration, those having diameters ranging from 2 to 4 mm may be employed for coronary bypass, those having diameters ranging from 2 to 10 mm, may be employed peripheral vascular grafts, those having diameters ranging from 20 to 50 mm and above may be employed for endovascular and endoluminal vascular grafts, other tubular prosthesis such as esophageal and colonic prosthesis, and so forth.

For tubular structures made using a rotating mandrel, the inside diameter will depend upon the size of the mandrel, with a typical mandrel diameter range ranging from 5 mm or less to 50 mm or more as noted above. Larger diameter mandrels are also suitable, for example, for forming tubular articles, which may be cut into sheets or otherwise shaped for making two-dimensional (open) structures such as patches and scaffolds.

More complex hollow structures may also be formed. For example, by selecting a tapered (i.e., with a gradual diameter change) or stepped (i.e., with an abrupt diameter change) mandrel, a tapered or stepped tubular structure is readily produced. Even more complex structures may be formed using mandrels that may be dissolved, melted, deflated or other otherwise reduced in size for removal after the structure is formed.

Although it is clear from the above discussion that the present invention is applicable to a wide variety of medical devices, a covered stent will now be described in more detail with reference to FIGS. 5 and 6.

Figure 5:
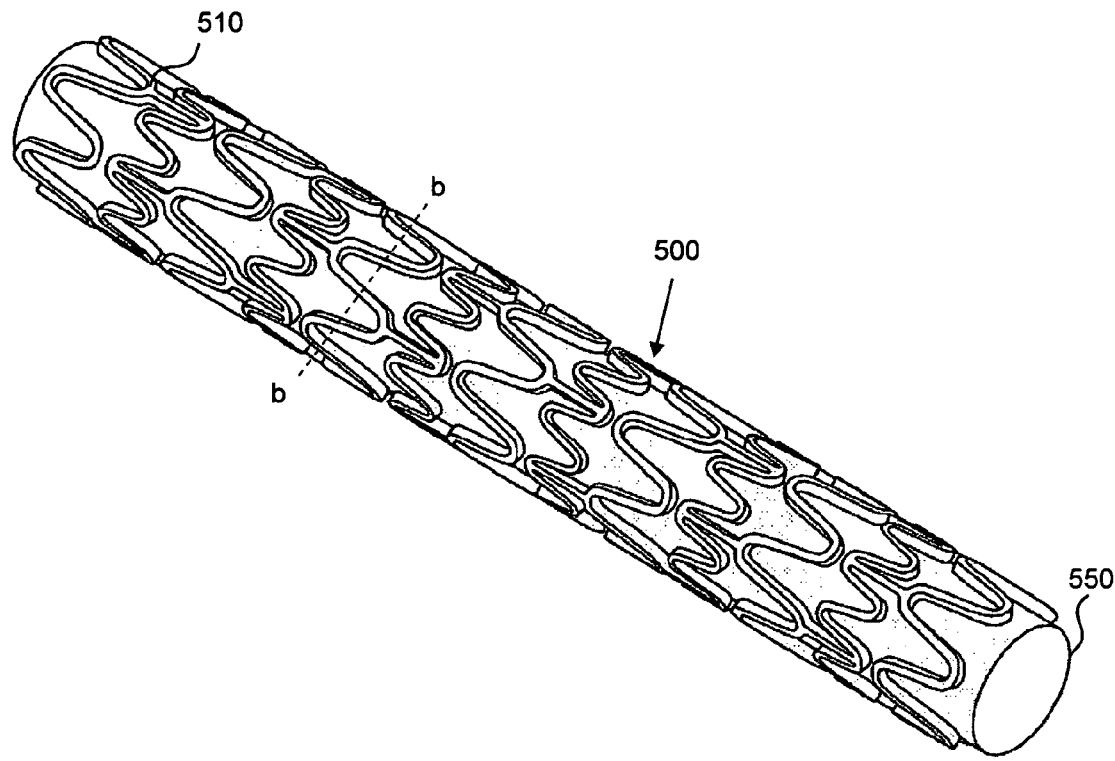
FIG. 5 is a perspective view of a known stent, arranged on a support.

Referring now to FIG. 5, a stent 500, like that illustrated in U.S. Application Publication No. 2005/0182480, is shown disposed on a support 550. The stent comprises various interconnected stent elements 510, which form numerous open cells 520.

Figure 6:
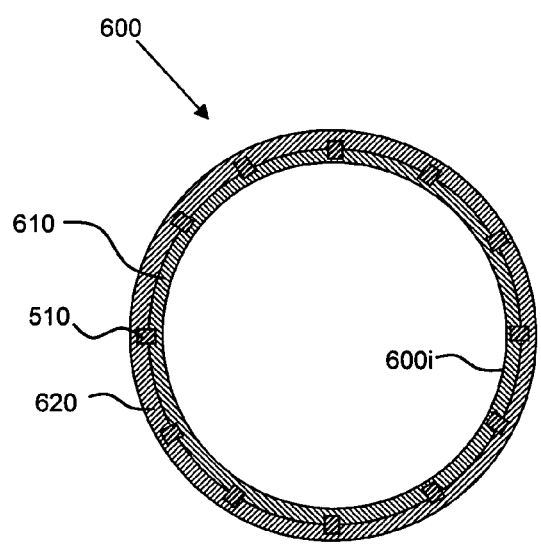
FIG. 6 is schematic cross-sectional view of the stent of FIG. 5, taken along the plane corresponding to line b-b, after the addition of inner and outer fibrous layers, in accordance with an embodiment of the present invention.

In FIG. 6, the device of FIG. 5 is shown in schematic cross-section, taken along the plane corresponding to line b-b, and after the addition of an inner fibrous layer 610 and an outer fibrous layer 620 in accordance with an embodiment of the present invention.

The inner fibrous layer 610, the outer fibrous layer 620, or both, may contain a multicomponent fiber, which, in turn, may be formed from polymeric components that are biostable, polymeric components that are biodegradable, or a polymeric component that is biostable and another component that is biodegradable, several examples of which are given above. Inner fibrous layer 610, the outer fibrous layer 620 are also elastomeric, thereby allowing for the expansion of the stent without damage to the layers 610,620. They may also be water soluble and removable to help reduce diameter in some embodiments.

In the particular embodiment shown, the inner and outer fibrous layers 610 and 620 may be formed of dry spun SIBS copolymer fibers ranging from 300 nanometers to 100 micrometers in diameter, and may have a thicknesses ranging from 1 to 500 micrometers and pore sizes ranging from 10 to 50 micrometers.

A structure like that of FIG. 6 may be made, for example, by first forming an inner layer of multi-component fiber 610 on a mandrel, followed by placement of the stent 500 of FIG. 5 snugly over the inner fibrous layer 610 (e.g., compressing as needed), followed by the formation of an outer layer of multi-component fiber 620 over the stent 500. Bonding between the inner 610 and outer 620 layers (through the open cells of the stent) may be established by various mechanisms including, for example, the presence of sufficient solvent in the fiber forming the outer layer 620 (e.g., where a dry spinning process is employed), the presence of sufficient heat in the fiber forming the outer layer 620 (e.g., where a melt spinning process is employed), the application of an adhesive layer prior to application of the outer layer 620, thermal fusion between the layers 610,620 after the application of the outer layer 620 (e.g., where the inner and/or outer layers have thermoplastic character), and so forth.

Polymers which may be employed for forming fiber components, barrier layers, substrates, reinforcing elements, and so forth in accordance with the present invention will now be set forth in more detail. Such polymers may vary widely and include, for example, suitable members selected from the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides and polyether block amides, polyamidimides, polyesterimides, and polyetherimides; polysulfone polymers and copolymers including polyarylsulfones and polyethersulfones; polyamide polymers and copolymers including nylon 6,6, nylon 12, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinyl acetate copolymers (EVA), polyvinylidene chlorides, polyvinyl ethers such as polyvinyl methyl ethers, polystyrenes, styrene-maleic anhydride copolymers, vinyl-aromatic-olefin copolymers, including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene and polystyrene-polyisobutylene-polystyrene block copolymers such as those disclosed in U.S. Pat. No. 6,545,097 to Pinchuk), polyhedral oligomeric silsesquioxane (POSS) containing polymers, polyvinyl ketones, polyvinylcarbazoles, and polyvinyl esters such as polyvinyl acetates; polybenzimidazoles; ethylene-methacrylic acid copolymers and ethylene-acrylic acid copolymers, where some of the acid groups can be neutralized with either zinc or sodium ions (commonly known as ionomers); polyalkyl oxide polymers and copolymers including polyethylene oxides (PEO); polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of poly(lactic acid) and poly(caprolactone) is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-co-methylacrylates such as ethylene-methyl methacrylate copolymers, and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF), including elastomeric copolymers of vinylidene fluoride and hexafluoropropylene; silicone polymers and copolymers; thermoplastic polyurethanes (TPU); elastomers such as elastomeric polyurethanes and polyurethane copolymers (including block and random copolymers that are polyether based, polyester based, polycarbonate based, aliphatic based, aromatic based and mixtures thereof; examples of commercially available polyurethane copolymers include Bionate®, Carbothane®, Tecoflex®), Tecothane®, Tecophilic®, Tecoplast®, Pellethane®, Chronothane® and Chronoflex®); p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and further copolymers of the above.

In certain embodiments, polymers are employed which are inherently charged, including polymers which are polycationic, polyanionic, or polyzwitterionic at a relevant pH (e.g., the pH at the implantation site). Such polymers typically have multiple (e.g., 5, 10, 25, 50, 100, or more, frequently, many more) charged sites. They include polyacids, polybases, polyacids-polybases, and polysalts, for example, polyelectrolytes, including ionomers (polyelectrolytes in which a small but significant proportion of the constitutional units carry charges).

Polyanionic polymers are employed in certain embodiments of the invention, because they are known to have enhanced biocompatibility in certain applications. Polyanionic polymers suitable for the practice of the invention may be natural or synthetic, they may be homopolymers or copolymers, and they may be used singly or in blends. Specific examples of polyanionic polymers may be selected, for example, from suitable members of the following: (a) polysulfonates such as polyvinylsulfonates, poly(styrenesulfonates) such as poly(sodium styrenesulfonate) (PSS), sulfonated poly(tetrafluoroethylene), sulfonated polymers such as those described in U.S. Pat. No. 5,840,387, including sulfonated styrene-ethylene/butylene-styrene triblock copolymers, sulfonated styrenic homopolymers and copolymer such as a sulfonated versions of the polystyrene-polyolefin copolymers described in U.S. Pat. No. 6,545,097 to Pinchuk et al., which polymers may be sulfonated, for example, using the processes described in U.S. Pat. Nos. 5,840,387 and 5,468,574, see also Yossef A. Elabd and Eugene Napadensky, "Sulfonation and characterization of poly(styrene-isobutylene-styrene) triblock copolymers at high ion-exchange capacities," *Polymer* 45 (2004) 3037-3043, as well as sulfonated versions of various other homopolymers and copolymers, (b) polycarboxylates such as acrylic acid polymers and salts thereof (e.g., ammonium, potassium, sodium, and so forth salts), for instance, those available from Atofina and Polysciences Inc., methacrylic acid polymers and salts thereof (e.g., EUDRAGIT, a methacrylic acid and ethylacrylate copolymer), carboxymethylcellulose, carboxymethylamylose and carboxylic acid derivatives of various other polymers, polyanionic peptides and proteins such as glutamic acid polymers and copolymers, aspartic acid polymers and copolymers, and gelatin, (c) polyphosphates such as phosphoric acid derivatives of various polymers, (d) polyphosphonates such as polyvinylphosphonates, (e) polysulfates such as polyvinylsulfates, and so forth.

Certain beneficial polymers for use in the present invention are block copolymers. For example, block copolymers may be employed which contain (a) one or more low $T_g$ polymer blocks and (b) one or more high $T_g$ polymer blocks. Certain block copolymers having low and high $T_g$ polymer blocks are known to possess many interesting physical properties due to the presence of a low $T_g$ phase, which is soft and elastomeric at body temperature, and a high $T_g$ phase, which is hard at body temperature. As used herein, "low $T_g$ polymer blocks" are those that display a $T_g$ that is below body temperature, more typically 20° C. to 0° C. to −25° C. to −50° C. or below. Conversely, as used herein, elevated or "high $T_g$ polymer blocks" are those that display a glass transition temperature that is above body temperature, more typically 50° C. to 75° C. to 100° C. or above. $T_g$ can be measured by differential scanning calorimetry (DSC).

Block copolymer configurations may vary widely and include, for example, the following configurations (in which high $T_g$ polymer chains, H, and low $T_g$ polymer chains, L, are used for illustrative purposes, although other blocks having different characteristics can clearly be substituted), among others: (a) block copolymers having alternating chains of the type $(HL)_m$, $L(HL)_m$ and $H(LH)_m$ where m is a positive whole number of 1 or more, (b) multiarm copolymers such as $X(LH)_n$, and $X(HL)_n$, where n is a positive whole number of 2 or more, and X is a hub species (e.g., an initiator molecule residue, a residue of a molecule to which preformed polymer chains are attached, etc.), and (c) comb copolymers having an L chain backbone and multiple H side chains and vice versa (i.e., having an H chain backbone and multiple L side chains).

Specific examples of low $T_g$ polymer chains include homopolymer and copolymer chains containing one or more of the following (listed along with published $T_g$'s for homopolymers of the same): (1) acrylic monomers including: (a) alkyl acrylates such as methyl acrylate ($T_g$ 10° C.), ethyl acrylate ($T_g$ −24° C.), propyl acrylate, isopropyl acrylate ($T_g$ −11° C., isotactic), butyl acrylate ($T_g$ −54° C.), sec-butyl acrylate ($T_g$ −26° C.), isobutyl acrylate ($T_g$ −24° C.), cyclohexyl acrylate ($T_g$ 19° C.), 2-ethylhexyl acrylate ($T_g$ −50° C.), dodecyl acrylate ($T_g$ −3° C.) and hexadecyl acrylate ($T_g$ 35° C.), (b) arylalkyl acrylates such as benzyl acrylate ($T_g$ 6° C.), (c) alkoxyalkyl acrylates such as 2-ethoxyethyl acrylate ($T_g$ −50° C.) and 2-methoxyethyl acrylate ($T_g$ −50° C.), (d) haloalkyl acrylates such as 2,2,2-trifluoroethyl acrylate ($T_g$ −10° C.) and (e) cyano-alkyl acrylates such as 2-cyanoethyl acrylate ($T_g$ 4° C.); (2) methacrylic monomers including (a) alkyl methacrylates such as butyl methacrylate ($T_g$ 20° C.), hexyl methacrylate ($T_g$ −5° C.), 2-ethylhexyl methacrylate ($T_g$ −10° C.), octyl methacrylate ($T_g$ −20° C.), dodecyl methacrylate ($T_g$ −65° C.), hexadecyl methacrylate ($T_g$ 15° C.) and octadecyl methacrylate ($T_g$ −100° C.) and (b) aminoalkyl methacrylates such as diethylaminoethyl methacrylate ($T_g$ 20° C.) and 2-tert-butyl-aminoethyl methacrylate ($T_g$ 33° C.); (3) vinyl ether monomers including (a) alkyl vinyl ethers such as ethyl vinyl ether ($T_g$ −43° C.), propyl vinyl ether ($T_g$ −49° C.), butyl vinyl ether ($T_g$ −55° C.), isobutyl vinyl ether ($T_g$ −19° C.), 2-ethylhexyl vinyl ether ($T_g$ −66° C.) and dodecyl vinyl ether ($T_g$ −62° C.); (4) cyclic ether monomers include tetrahydrofuran ($T_g$ −84° C.), trimethylene oxide ($T_g$ −78° C.), ethylene oxide ($T_g$ −66° C.), propylene oxide ($T_g$ −75° C.), methyl glycidyl ether ($T_g$ −62° C.), butyl glycidyl ether ($T_g$ −79° C.), allyl glycidyl ether ($T_g$ −78° C.), epibromohydrin ($T_g$ −14° C.), epichlorohydrin ($T_g$ −22° C.), 1,2-epoxybutane ($T_g$ −70° C.), 1,2-epoxyoctane ($T_g$ −67° C.) and 1,2-epoxydecane ($T_g$ −70° C.); (5) ester monomers (other than acrylates and methacrylates) including ethylene malonate ($T_g$ −29° C.), vinyl acetate ($T_g$ 30° C.), and vinyl propionate ($T_g$ 10° C.); (6) alkene monomers including ethylene, propylene ($T_g$ −8 to −13° C.), isobutylene ($T_g$ −73° C.), 1-butene ($T_g$ −24° C.), trans-butadiene ($T_g$ −58° C.), 4-methyl pentene ($T_g$ 29° C.), 1-octene ($T_g$ −63° C.) and other α-olefins, cis-isoprene ($T_g$ −63° C.), and trans-isoprene ($T_g$ −66° C.); (7) halogenated alkene monomers including vinylidene chloride ($T_g$ −18° C.), vinylidene fluoride ($T_g$ −40° C.), cis-chlorobutadiene ($T_g$ −20° C.), and trans-chlorobutadiene ($T_g$ −40° C.); and (8) siloxane monomers including dimethylsiloxane ($T_g$ −127° C.), diethylsiloxane, methylethylsiloxane, methylphenylsiloxane ($T_g$ −86° C.), and diphenylsiloxane.

Specific examples of high $T_g$ polymer chains include homopolymer and copolymer chains containing one or more of the following: (1) vinyl aromatic monomers including (a) unsubstituted vinyl aromatics, such as styrene ($T_g$ 100° C.) and 2-vinyl naphthalene ($T_g$ 151° C.), (b) vinyl substituted aromatics such as a-methyl styrene, and (c) ring-substituted vinyl aromatics including ring-alkylated vinyl aromatics such as 3-methylstyrene ($T_g$ 97° C.), 4-methylstyrene ($T_g$ 97° C.), 2,4-dimethylstyrene ($T_g$ 112° C.), 2,5-dimethylstyrene ($T_g$ 143° C.), 3,5-dimethylstyrene ($T_g$ 104° C.), 2,4,6-trimethylstyrene ($T_g$ 162° C.), and 4-tert-butylstyrene ($T_g$ 127° C.), ring-alkoxylated vinyl aromatics, such as 4-methoxystyrene ($T_g$ 113° C.) and 4-ethoxystyrene ($T_g$ 86° C.), ring-halogenated vinyl aromatics such as 2-chlorostyrene ($T_g$ 119° C.), 3-chlorostyrene ($T_g$ 90° C.), 4-chlorostyrene ($T_g$ 110° C.), 2,6-dichlorostyrene ($T_g$ 167° C.), 4-bromostyrene ($T_g$ 118° C.) and 4-fluorostyrene ($T_g$ 95° C.) and ring-ester-substituted vinyl aromatics such as 4-acetoxystyrene ($T_g$ 116° C.); (2) other vinyl monomers including (a) vinyl esters such as vinyl benzoate ($T_g$ 71° C.), vinyl 4-tert-butyl benzoate ($T_g$ 101° C.), vinyl cyclohexanoate ($T_g$ 76° C.), vinyl pivalate ($T_g$ 86° C.), vinyl trifluoroacetate ($T_g$ 46° C.), vinyl butyral ($T_g$ 49° C.), (b) vinyl amines such as 2-vinyl pyridine ($T_g$ 104° C.), 4-vinyl pyridine ($T_g$ 142° C.), and vinyl carbazole ($T_g$ 227° C.), (c) vinyl halides such as vinyl chloride ($T_g$ 81° C.) and vinyl fluoride ($T_g$ 40° C.); (d) alkyl vinyl ethers such as tert-butyl vinyl ether ($T_g$ 88° C.) and cyclohexyl vinyl ether ($T_g$ 81° C.), and (e) other vinyl compounds such as vinyl ferrocene ($T_g$ 189° C.); (3) other aromatic monomers including acenaphthalene ($T_g$ 214° C.) and indene ($T_g$ 85° C.); (4) methacrylic monomers including (a) methacrylic acid anhydride ($T_g$ 159° C.), (b) methacrylic acid esters (methacrylates) including (i) alkyl methacrylates such as methyl methacrylate ($T_g$ 105-120° C.), ethyl methacrylate ($T_g$ 65° C.), isopropyl methacrylate ($T_g$ 81° C.), isobutyl methacrylate ($T_g$ 53° C.), t-butyl methacrylate ($T_g$ 118° C.) and cyclohexyl methacrylate ($T_g$ 92° C.), (ii) aromatic methacrylates such as phenyl methacrylate ($T_g$ 110° C.) and including aromatic alkyl methacrylates such as benzyl methacrylate ($T_g$ 54° C.), (iii) hydroxyalkyl methacrylates such as 2-hydroxyethyl methacrylate ($T_g$ 57° C.) and 2-hydroxypropyl methacrylate ($T_g$ 76° C.), (iv) additional methacrylates including isobornyl methacrylate ($T_g$ 110° C.) and trimethylsilyl methacrylate ($T_g$ 68° C.), and (c) other methacrylic-acid derivatives including methacrylonitrile ($T_g$ 120° C.); (5) acrylic monomers including (a) certain acrylic acid esters such as tert-butyl acrylate ($T_g$ 43-107° C.), hexyl acrylate ($T_g$ 57° C.) and isobornyl acrylate ($T_g$ 94° C.); and (b) other acrylic-acid derivatives including acrylonitrile ($T_g$ 125° C.).

More specific examples of beneficial block copolymers include those having polyalkylene blocks and poly(vinyl aromatic) blocks, such as block copolymers containing polyisobutylene and polystyrene blocks, for example, polystyrene-polyisobutylene-polystyrene triblock copolymers (SIBS copolymers), described in U.S. Pat. No. 6,545,097 to Pinchuk et al., which is hereby incorporated by reference in its entirety. These copolymers have proven to be valuable elastomers for use implantable or insertable medical device applications due to their excellent strength, biocompatibility and biostability.

In accordance with certain embodiments of the present invention, a dry spinning technique is employed in which a solution containing styrene-isobutylene copolymer is spun as a component of a multi-component fiber. Further details regarding dry spinning of styrene-isobutylene copolymers, may be found in copending, commonly assigned U.S. Ser. No. 10/801,228.

As indicated above, one or more therapeutic agents are provided within the medical devices of the invention in certain embodiments. Taking a fibrous layer as an example, one or more therapeutic agents may be: (a) provided within the fibers making up the layer (e.g., by providing the therapeutic agent(s) within the polymeric fluid that forms the fibers as previously described, or by applying a solution containing the therapeutic agent(s) to a previously formed fiber), (b) covalently or non-covalently bound to the surface of the fibers before forming a fibrous region from the same (e.g. by providing the therapeutic agent(s) within a coating that is sprayed or otherwise provided on the fibers, etc.), (c) covalently or non-covalently bound to the surface of the fibrous region after it is formed (e.g., by providing the therapeutic agent(s) within a coating that is sprayed or otherwise provided on the fibrous region, such as a polymeric barrier layer, etc.), and so forth.

A wide range of therapeutic agent loadings may be used in conjunction with the medical devices of the present invention, with the pharmaceutically effective amount being readily determined by those of ordinary skill in the art and ultimately depending, for example, on the nature of the therapeutic agent(s), the environment into which the medical device is introduced, and the nature of the association between the therapeutic agent(s) and the medical device, among other factors.

Therapeutic agents for use in the medical devices of the invention include genetic and non-genetic therapeutic agents as well as cells. Exemplary non-genetic biologically active agents for use in connection with the present invention may be selected from suitable members of the following: (a) antithrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (1) antimicrobial agents such as triclosan, cephalosporins, antimicrobial peptides such as magainins, aminoglycosides and nitrofurantoin; (m) cytotoxic agents, cytostatic agents and cell proliferation affectors; (n) vasodilating agents; (o)agents that interfere with endogenous vasoactive mechanisms, (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) beta-blockers, (u) bARKct inhibitors, (v) phospholamban inhibitors, (w) Serca 2 gene/protein, (x) immune response modifiers including aminoquizolines, for instance, imidazoquinolines such as resiquimod and imiquimod, (y) human apolioproteins (e.g., AI, AII, AIII, AIV, AV, etc.).

Further non-genetic therapeutic agents, not necessarily exclusive of the foregoing, from which suitable agents for the practice of the present invention may be selected include the following: paclitaxel (including particulate forms thereof, for instance, protein-bound paclitaxel particles such as albumin-bound paclitaxel nanoparticles, e.g., ABRAXANE), sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, and Ridogrel, beta-blockers, bARKct inhibitors, phospholamban inhibitors, Serca 2 gene/protein, imiquimod, human apolioproteins (e.g., AI-AV), growth factors (e.g., VEGF-2), as well a derivatives of the forgoing, among others.

Other non-genetic agents include radioactive materials.

Suitable genetic therapeutic agents for the practice of the present invention may be selected, for example, from the following: anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor $\alpha$ and $\beta$, platelet-derived endothelial growth factor, platelet-derived growth factor, tumor necrosis factor $\alpha$, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Suitable cells for the practice of the present invention may be selected, for example, from the following: cells of human origin (autologous or allogeneic), including whole bone marrow, bone marrow derived mono-nuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous biologically active agents, not necessarily exclusive of those listed above, have been identified as candidates for vascular treatment regimens, for example, as agents targeting restenosis. Suitable agents for the practice of the present invention may therefore be selected from the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including $\alpha$-antagonists such as prazosin and bunazosine, $\beta$-antagonists such as propranolol and $\alpha/\beta$-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and $\beta$-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-$\beta$ pathway agents such as polyanionic agents (heparin, fucoidin), decorin, and TGF-$\beta$ antibodies, EGF pathway agents such as EGF antibodies, receptor antagonists and chimeric fusion proteins, TNF-$\alpha$ pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional biologically active agents useful for the practice of the present invention are also disclosed in U.S. Pat. No. 5,733,925 assigned to NeoRx Corporation, the entire disclosure of which is incorporated by reference.

Although various embodiments are specifically illustrated and described herein, it will be appreciated that modifications and variations of the present invention are covered by the above teachings and are within the purview of the appended claims without departing from the spirit and intended scope of the invention.

What is claimed is:

1. A medical device comprising a metallic substrate and a fibrous layer disposed over said substrate, said fibrous layer comprising a multi-component polymeric fiber which comprises a first component comprising a first polymer and a second component comprising a second polymer that differs from said first polymer, said multi-component polymeric fiber further comprising a therapeutic agent wherein:
    a) said first component extends to an outside surface of said fiber and said second component is internal to said fiber;
    b) said first component comprises a water-swellable polymer; and
    c) said second component comprises a biostable polymer.

2. The medical device of claim 1, wherein said fibrous layer comprises a plurality of said fibers.

3. The medical device of claim 1, wherein said fibrous layer is a coating layer disposed over a medical device.

4. The medical device of claim 1, wherein said metallic substrate comprises a filamentous reinforcement element.

5. The medical device of claim 1, wherein said metallic substrate comprises multiple reinforcement elements.

6. The medical device of claim 1, wherein said multi-component polymeric fiber is a melt spun fiber.

7. The medical device of claim 1, wherein said multi-component polymeric fiber is a solvent spun fiber.

8. The medical device of claim 1, wherein said first component is biodegradable.

9. The medical device of claim 1, wherein said first component is biostable.

10. The medical device of claim 1, wherein said first polymer comprises a monomer not found in said second polymer.

11. The medical device of claim 1, wherein said first component comprises an additional polymer, wherein said second component comprises an additional polymer, or wherein said first component and said second component each comprises an additional polymer.

12. The medical device of claim 1, wherein said first component comprises a therapeutic agent and said second component does not comprise a therapeutic agent.

13. The medical device of claim 1, wherein said multi-component polymeric fiber comprises first and second therapeutic agents that differ from one another.

14. The medical device of claim 1, wherein said multi-component polymeric fiber comprises an antithrombotic agent and an antiproliferative agent.

15. The medical device of claim 1, wherein said multi-component polymeric fiber comprises first, second and third therapeutic agents that differ from one another.

16. The medical device of claim 1, wherein said multi-component polymeric fiber comprises an antithrombotic agent, an antiproliferative agent, and an endothelialization facilitator.

17. The medical device of claim 1, wherein said first component comprises first and second therapeutic agents that differ from one another.

18. The medical device of claim 1, wherein said first component comprises a first therapeutic agent, wherein said second component comprises a second therapeutic agent, and wherein said first and second therapeutic agents may be the same or different.

19. The medical device of claim 1, wherein said first and second components are arranged in a sheath/core fiber structure or an islands-in-the-sea fiber structure.

20. The medical device of claim 1, further comprising a third component comprising a third polymer that differs from said first and second polymers.

21. The medical device of claim 1, wherein said fiber has a diameter between 100 nm and 10 microns.

22. The medical device of claim 1, wherein said medical device comprises a woven fibrous layer.

23. The medical device of claim 1, wherein said medical device comprises a non-woven fibrous layer.

24. The medical device of claim 1, wherein said medical device is selected from hernia repair patches, gastrointestinal tract patches, uro-gynecological tract patches, vascular access ports, fabric to join devices to human arteries, wound dressings, membranes, anterior cruciate ligaments, neurovascular aneurysm treatment articles, valve leaflets for heart valves, valve leaflets for venous valves, balloons, catheter shafts, guidewires, stents, stent grafts, gastrointestinal tract grafts, uro-gynecological tract grafts, coronary vascular grafts, peripheral vascular grafts, arterio-venous access grafts, embolic filters, scaffolds for tissue engineering, guidewires, pacemakers, and artificial hearts.

25. The medical device of claim 1, wherein said metallic substrate is a stent, wherein said fibrous layer is disposed over an abluminal surface of the stent and wherein a luminal surface of said stent is bare metal.

26. The medical device of claim 1, wherein the water-swellable polymer is a thermoplastic hydrogel.

27. The medical device of claim 1, wherein the second component comprises a block copolymer.

28. The medical device of claim 27, wherein the block copolymer comprises a high Tg polymer block and a low Tg polymer block.

29. The medical device of claim 1, wherein the first component comprises an anti-thrombotic agent and the second component comprises an antiproliferative agent.

30. The medical device of claim 1, further comprising a third component, wherein a) the first component comprises a bioactive agent, b) the second component comprises an antifouling agent and c) the third component comprises an antiproliferative agent.

31. The medical device of claim 1, further comprising a third component, wherein the first and third components each independently comprises a biodegradable polymer.

32. The medical device of claim 1, further comprising a third component, wherein the first component comprises a biostable polymer and the third component comprises a biodegradable polymer or a hydrogel polymer.

33. The medical device of claim 1, wherein said fibrous layer is elastomeric.

34. The medical device of claim 1, wherein said first component comprises a swellable hydrogel.

35. The medical device of claim 1, wherein said second component comprises a triblock copolymer having a polyisobutylene midblock and polystyrene end blocks.

* * * * *